United States Patent [19]

Aoki et al.

[11] 4,115,439
[45] Sep. 19, 1978

[54] PROCESS FOR THE PREPARATION OF OPTICALLY ACTIVE α-PHENYLGLYCINE AND INTERMEDIATES THEREOF

[75] Inventors: Shigeru Aoki, Tokyo; Yasuhisa Tashiro, Yokohama; Yuzo Aboshi, Tokyo; Toshiro Narita, Shima; Tadashi Shirai, Musashino, all of Japan

[73] Assignee: Nippon Kayaku Kabushiki Kaisha, Tokyo, Japan

[21] Appl. No.: 670,420

[22] Filed: Mar. 25, 1976

[30] Foreign Application Priority Data

Mar. 27, 1975 [JP] Japan .................................. 50-36070

[51] Int. Cl.² .................... C07C 101/04; C07C 143/26
[52] U.S. Cl. ................................ 562/402; 260/501.12
[58] Field of Search ........................ 260/501.12, 518 R

[56] References Cited

U.S. PATENT DOCUMENTS

| B 544,899 | 2/1976 | Shirai ..................................... 260/501 |
| 3,933,902 | 1/1976 | Watanabe et al. ............... 260/501.12 |

OTHER PUBLICATIONS

Nagai et al., Chem. Abstracts, vol. 78, 16478(h) (1973).

Primary Examiner—James O. Thomas, Jr.
Assistant Examiner—G. T. Breitenstein
Attorney, Agent, or Firm—Russell & Nields

[57] ABSTRACT

DL- α-phenylglycine can be combined with benzenesulfonic acid, p-ethylbenzenesulfonic acid or m-xylenesulfonic acid to give the salt. The salt of the racemate may be more soluble in a sulfuric acid solution than the salt of the optically active isomer by suitably choosing the concentration of the sulfuric acid solution, and then the optical resolution by fractional crystallization is carried out. The D- or L- α-phenylglycine sulfonate is easily liberated of the sulfonic acid portion to give optically active D- or L- α-phenylglycine.

3 Claims, 3 Drawing Figures

PROCESS FOR THE PREPARATION OF OPTICALLY ACTIVE α-PHENYLGLYCINE AND INTERMEDIATES THEREOF

FIELD OF THE INVENTION

This invention relates to a novel process for the production of optically active D- and L-α-phenylglycine and intermediates thereof. More particularly, this invention pertains to a novel process for the production of optically active D- and L-α-phenylglycine and intermediates thereof which comprises optically resolving a DL-α-phenylglycine sulfonate having the general formula:

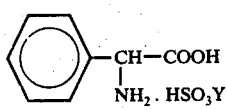

wherein Y represents a member selected from the group consisting of phenyl, p-ethylphenyl and m-xylyl in a sulfuric acid solution and liberating the sulfonic acid portion from the thus obtained salts of the optically active isomers to obtain the respective optically active isomers.

BACKGROUND OF THE INVENTION

The optical resolution of DL-α-phenylglycine has been known for many years as the commercial practice to form diastereomers with d-camphor-sulfonic acid. Also, the preferential crystallization is known to form ammonium salts (Japanese Patent Publication No. 45,388/74) or monoethylamine salts (Japanese Patent Laid-Open Publication No. 29,715/73) of N-acetyl-α-phenylglycine. These prior art methods, however, have serious drawbacks in that the former method employs d-camphor which is an expensive natural substance, while the latter method takes a complicated pathway, that is, an α-phenylglycine racemate is converted into an acetyl derivative thereof which is resolved into two isomers, each of which must, in turn, be subjected to hydrolysis of the acetyl groups.

In addition, the optical resolution of salts obtained by some amino acid with aromatic sulfonic acid derivatives have been proposed. In the case of DL-α-phenylglycine, however, its sulfonates are generally only slightly soluble in water and cannot be applied to the optical resolution. Recently, the optical resolution for the benzenesulfonate of DL-α-phenylglycine has been proposed only in an aqueous benzenesulfonic acid solution. (Ger. offen 23/9493/74)

SUMMARY OF THE INVENTION

To overcome various disadvantages accompanied with the optical resolution of DL-α-phenylglycine the inventors made a precise study on the resolution of salts of DL-α-phenylglycine with a sulfonic acid by fractional crystallization and have found the fact that α-phenylglycine can be combined with benzenesulfonic acid, m-xylenesulfonic acid and p-ethylbenzenesulfonic acid to form salts, respectively, and such salts of the racemate are more soluble in an aqueous solution of sulfuric acid than the salts of the optically active isomers under the specific conditions, details of which are described hereinafter. Consequently, either D- or L-α-phenylglycine (optically active isomer) sulfonate can easily be separated from the DL-α-phenylglycine sulfonate in the sulfuric acid solution by fractional crystallization.

DETAILED DESCRIPTION

The above-disclosed facts on which the present invention is based will be illustrated more exactly with reference to the accompanying drawing.

Figure 1:
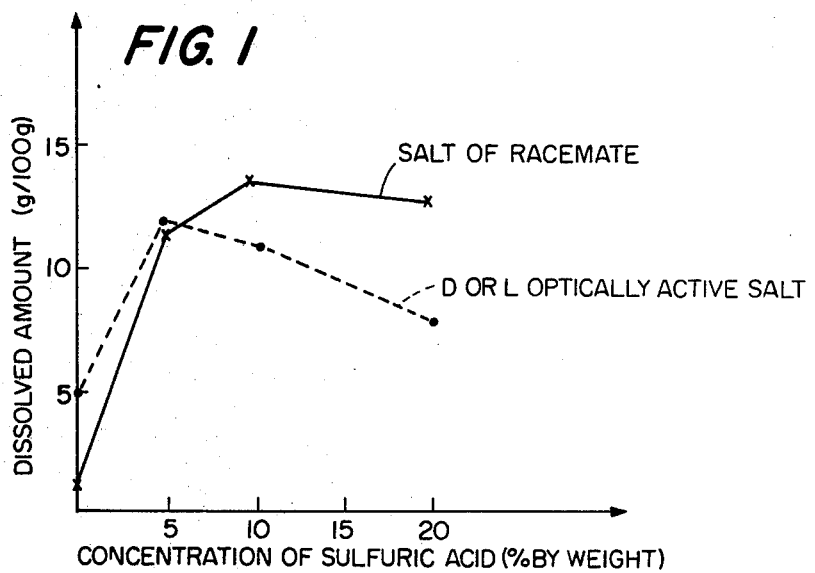
FIG. 1 is a graph showing the solubilities of the salts of α-phenylglycine with benzenesulfonic acid in an aqueous solution of sulfuric acid at 30° C.
Figure 2:
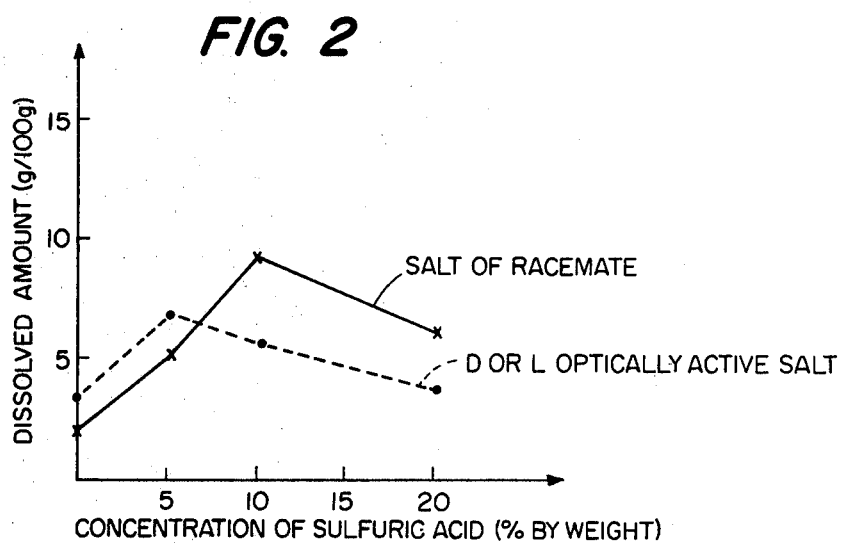
FIG. 2 is a graph showing the solubilities of the salts of α-phenylglycine with p-ethylbenzenesulfonic acid in an aqueous solution of sulfuric acid at 30° C.
Figure 3:
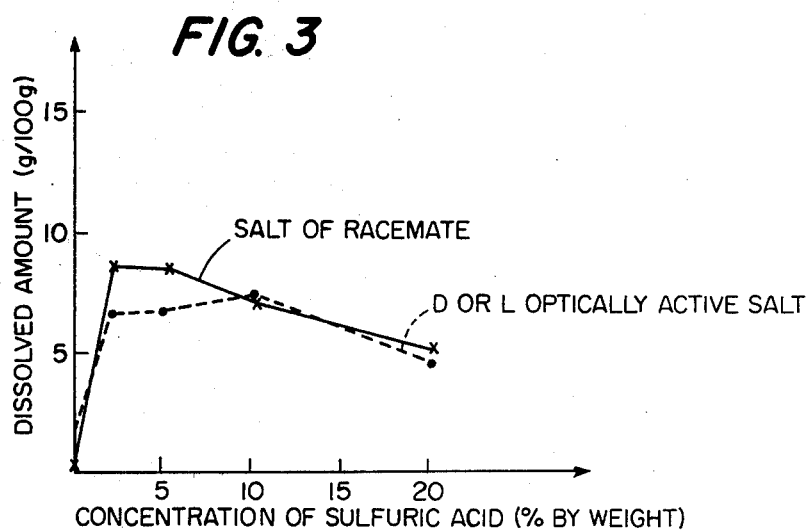
FIG. 3 is a graph showing the solubilities of the salts of α-phenylglycine with m-xylenesulfonic acid in an aqueous solution of sulfuric acid at 30° C.

In the solubility diagrams of FIGS. 1 through 3 a solid line represents the solubility of the salt of the racemate and a dotted line the solubility of the salt of the optically active (D- or L-) isomer. The concentration of sulfuric acid in the aqueous solution is plotted as abscissa in terms of percent by weight and the solubility of the salts as ordinate in terms of grams per 100 grams of the solution.

More precisely, in FIG. 1 the solubilities of DL-α-phenylglycine benzenesulfonate and D- or L-α-phenylglycine benzenesulfonate are plotted against the sulfuric acid concentration. In FIG. 2 the solubilities of DL-α-phenylglycine · p-ethylbenzenesulfonate and D- or L-α-phenylglycie · p-ethylbenzenesulfonate are plotted against the sulfuric acid concentration. In FIG. 3 the solubilities of DL-α-phenylglycine · m-xylenesulfonate and D- or L-α-phenylglycine · m-xylenesulfonate are plotted against the sulfuric acid concentration.

It is apparent from FIGS. 1 to 3 that the salts of α-phenylglycine with sulfonic acids exert a change in solubility depending upon the sulfuric acid concentration. FIGS. 1 through 3 show that the salt of the racemate is more soluble than the salt of the optically active isomer at concentrations of the sulfuric acid solution in the range of more than 6.0 wt% for benzenesulfonic acid, more than 6.9 wt% for p-ethylbenzenesulfonic acid, or between 0.9wt% and 9.0 wt% for m-xylenesulfonic acid. This higher solubility of the racemate permits the optical resolution by fractional crystallization. Therefore, the feature of the present invention resides in that a salt of α-phenylglycine with one of the above-described three sulfonic acids can be optically resolved by fractional crystallization from the sulfuric acid solution having concentrations from 1 wt% to 50 wt%.

In carrying out the invention, first a supersaturated solution of a salt of DL-α-phenylglycine with a sulfonic acid selected from the above three is prepared. To this end, a salt of the racemate or its mixture with a salt of either one of the optically active isomers (i.e., mixture containing an excess of an optically active isomer salt) is added to a sulfuric acid solution having any desired concentration (e.g., an aqueous solution containing 20 wt% of sulfuric acid in the case of DL-α-phenylglycine-benzenesulfonate), while stirring and heating to completely dissolve the salt. The thus obtained saturated solution may be cooled or condensed. The resulting supersaturated solution is then seeded with the salt of the desired optically active isomer. The salt of the optically active isomer corresponding to the seed crystals selectively crystallizes.

The seed crystals may preferably be added in a larger amount. The amount on the order of 0.1% by weight of the salt in the supersaturated solution may suffice. The crystallization may be carried out at a temperature of 0° to 50° C, preferably at room temperature because of easy handling.

As a solvent for the supersaturated solution, an aqueous solution of sulfuric acid which is most commercially available may be used. In place of water water-containing organic solvents such as aqueous methanol, aqueous ethanol and aqueous acetone may also be employed.

Since the salt of the optically active isomer obtained by the single crystallization does not have satisfactory optical purity, it may be recrystallized from another sulfuric acid solution having the same concentration as that used for the resolution, yielding purified crystals of the optically active isomer salt.

The resulting optically pure salt of α-phenylglycine with the sulfonic acid may be subjected to a conventional treatment for liberating the sulfonic acid portion. For example, a neutralization or ion exchange treatment can liberate the sulfonic acid portion from the salt. The result, is isolated optically active α-phenylglycine.

The salts, DL-α-phenylglycine · m-xylenesulfonate and DL-α-phenylglycine · p-ethylbenzenesulfonate and hence D- and L-α-phenylglycine · m-xylenesulfonate and D- and L-α-phenylglycine · p-ethylbenzenesulfonate are novel compounds. The former salts can easily be prepared by mixing equimolar amounts of DL-α-phenylglycine and m-xylenesulfonic acid or p-ethylbenzenesulfonic acid, adding water to the mixture and heating until in solution.

Among two optically active α-phenylglycine isomers obtained in accordance with the present invention D-α-phenylglycine is a very useful compound as a raw material for the synthesis of semisynthetic penicillins and cephalosporins.

The present invention will now be illustrated by the following Examples.

EXAMPLE 1

To a mixture of 3.0 g of DL-α-phenylglycine and 4.65 g of p-ethylbenzenesulfonic acid was added 10 g of water with heating until in solution. On cooling the solution to 5° C crystals of the DL-α-phenylglycine · p-ethylbenzenesulfonate precipitated. This precipitate was separated by filtration, washed with cold water and then dried. There was obtained 5.00 g of DL-α-phenylglycine · p-ethylbenzenesulfonate.
M.P.: 190° – 192° C
Elementary analysis
Calculated for $C_{16}H_{19}NSO_5$: C 56.96%; H 5.68%; N 4.15% Found: C 57.10%; H 5.69%; N 4.33%

EXAMPLE 2

To a mixture of 3.0 g of DL-α-phenylglycine and 5.55 g of m-xylenesulfonic acid dihydrate was added 10 g of water with heating until in solution. The same procedures as described in Example 1 were repeated. There was obtained 6.40 g of DL-α-phenylglycine · m-xylenesulfonate.
M.P.: 183° – 185° C
Elementary analysis
Calculated for $C_{16}H_{19}NSO_5$: C 56.96%; H 5.68%; N 4.15% Found: C 56.98%; H 5.70%; N 4.13%

EXAMPLE 3

To 200 g of 20% sulfuric acid were added 16.73 g of DL-α-phenylglycine, 0.88 g of D-α-phenylglycine and 20.50 g of benzenesulfonic acid with mixing and heating until in solution. The resulting solution was cooled to 31° C and then seeded with 0.10 g of D-α-phenylglycine benzenesulfonate at the indicated temperature. After stirring for one hour the solution was subjected to filtration, yielding 2.55 g of crude crystals of D-α-phenylglycine benzenesulfonate which had a specific rotation of $$[\alpha]_D^{20} = -66.31° \ (c = 2N \ HCl).$$

The crude crystals were dissolved in 2.31 g of 20% sulfuric acid. The recrystallization from this solution gave 2.21 g of pure crystals of D-α-phenylglycine benzenesulfonate which had a specific rotation of $$[\alpha]_D^{20} = -76.23° \ (c = 2N \ HCl).$$

A 2.00 g portion of the purified salt of the optically active D-isomer was neutralized with an aqueous solution of 3N sodium hydroxide, yielding 0.98 g of D-α-phenylglycine which had a specific rotation of $$[\alpha]_D^{20} = -157.2° \ (c = 1N \ HCl).$$

EXAMPLE 4

To 150 ml of 20% sulfonic acid were added 8.05 g of DL-α-phenylglycine, 0.89 g of D-α-phenylglycine and 11.18 g of p-ethylbenzenesulfonic acid with stirring and heating until in solution. The resulting solution was cooled to 28° C and then seeded with 0.1 g of D-α-phenylglycine · p-ethylbenzenesulfonate. After stirring for one hour the solution was subjected to filtration, yielding 2.76 g of crude crystals of D-α-phenylglycine · p-ethylbenzenesulfonate which had a specific rotation of $$[\alpha]_D^{20} = -58.73° \ (c = 2N \ HCl).$$

On recrystallization from the 20% sulfuric acid solution there was obtained 2.23 g of pure crystals of D-α-phenylglycine · p-ethylbenzenesulfonate.

$$[\alpha]_D^{20} = -70.43° \ (c = 2N \ HCl)$$

M.P. 200° – 202° C
Elementary analysis
Calculated for $C_{16}H_{19}NSO_5$: C 56.96%; H 5.68%; N 4.15% Found: C 56.93%; H 5.62%; N 4.17%
The purified salt was neutralized with an aqueous solution of 3N sodium hydroxide, yielding 1.00 g of D-α-phenylglycine which had a specific rotation of $$[\alpha]_D^{20} = -159.0° \ (c = 1N \ HCl),$$

EXAMPLE 5

To a mother liquor left after the crude crystals of D-α-phenylglycine · p-ethylbenzenesulfonate had been separated by filtration in Example 4 were added 0.75 g of DL-α-phenylglycine, 1.54 g of p-ethylbenzenesulfonic acid and 2.8 ml of 20% sulfuric acid with stirring and heating until in solution. The resulting solution was cooled to 28° C and then seeded with 0.1 g of L-α-phenylglycine-p-ethylbenzenesulfonate. After stirring for one hour the solution was subjected to filtration, yielding 2.98 g of crude crystals of L-α-phenylglycine · p-ethylbenzenesulfonate which had a specific rotation of $$[\alpha]_D^{20} = +67.24° \ (c = 2N \ HCl).$$

On recrystallization from the 20% sulfuric acid solution there was obtained 2.70 g of pure crystals of L-α-phenylglycine · p-ethylbenzenesulfonate $$[\alpha]_D^{20} = +70.45° \ (c = 2N \ HCl)$$

M.P. 200° – 201° C
Elementary analysis
Calculated for $C_{16}H_{19}NSO_5$: C 56.96%; H 5.68%; N 4.15% Found: C 56.90%; H 5.70%; N 4.16%

The purified salt was treated with an alkali in a similar manner as described in Example 4, yielding 1.15 g of L-α-phenylglycine which had a specific rotation of $$[\alpha]_D^{20} = +159.5° \ (c = 1N \ HCl).$$

EXAMPLE 6

To 162 ml of 2% sulfuric acid were added 15.08 g of DL-α-phenylglycine, 0.31 g of D-α-phenylglycine and 22.60 g of m-xylenesulfonic acid dihydrate with stirring and heating until in solution. The resulting solution was cooled to 35° C and then seeded with 0.05 g of D-α-phenylglycine · m-xylenesulfonate. After stirring for 20 minutes the solution was subjected to filtration, yielding 1.78 g of crude crystals of D-α-phenylglycine · m-xylenesulfonate which had a specific rotation of $$[\alpha]_D^{20} = -59.83° \ (c = 2N \ HCl).$$

On recrystallization from the 2% sulfuric acid solution there was obtained 1.42 g of pure crystals of D-α-phenylglycine · m-xylenesulfonate $$[\alpha]_D^{20} = -69.70° \ (c = 2N \ HCl)$$

M.P. 105° –107° C.
Elemental analysis
Calculated for $C_{16}H_{19}NSO_5 \cdot 2H_2O$: C 51.46%; H 6.21%; N 3.75% Found: C 51.42%; H 6.24%; N 3.73%

The purified salt was neutralized with an aqueous solution of 3N sodium hydroxide, yielding 0.62 g of D-α-phenylglycine.

EXAMPLE 7

To a mother liquor left after the crude crystals of D-α-phenylglycine · m-xylenesulfonate had been separated by filtration in Example 6 were added 0.81 g of DL-α-phenylglycine, 0.99 g of m-xylenesulfonic dihydrate acid and 0.8 ml of 2% sulfuric acid with stirring and heating until in solution. The resulting solution was cooled to 35° C and then seeded with 0.05 g of L-α-phenylglycine · m-xylenesulfonate. After stirring for 20 minutes the solution was subjected to filtration, yielding 1.81 g of crude crystals of L-α-phenylglycine · m-xylenesulfonate which had a specific rotation of $$[\alpha]_D^{20} = +64.40° \ (c = 2N \ HCl)$$

On recrystallization from the 2% sulfuric acid solution there was obtained 1.43 g of pure crystals of L-α-phenylglycine · m-xylenesulfonate.

$$[\alpha]_D^{20} = +70.00° \ (c = 2N \ HCl)$$

M.P. 105° –107° C
Elementary analysis
Calculated for $C_{16}H_{19}NSO_5 \cdot 2H_2O$: C 51.46%; H 6.21%; N 3.75% Found: C 51.42%; H 6.24%; N 3.73%

The purified salt was treated with an alkali in a similar manner as described in Example 6, yielding 0.67 g of L-α-phenylglycine.

Having thus described the principles of the invention, together with several illustrative embodiments thereof, it is to be understood that, although specific terms are employed, they are used in a generic and descriptive sense and not for purposes of limitation, the scope of the invention being set forth in the following claims:

We claim:

1. A process for producing optically active α-phenylglycine which comprises dissolving a DL-α-phenylglycine sulfonate having the general formula:

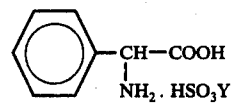

wherein Y represents a member selected from the group consisting of phenyl, p-ethylphenyl and m-xylyl in a 1 wt % to 50 wt % sulfuric acid solution to form a supersaturated solution thereof, adding at least 0.1% of seed crystals of an optically active D- or L-α-phenylglycine sulfonate to selectively crystallize the corresponding salt of the optically active isomer, separating the crystallized salt at 0° –50° C, and liberating the sulfonic acid portion from the salt to obtain the optically active isomer.

2. The process according to claim 1 wherein said supersaturated solution contains in excess either D- or L-α-phenylglycine sulfonate and then the seed crystals consist of the same isomer as that contained in excess.

3. The process according to claim 1 wherein said supersaturated solution of the DL-α-phenylglycine sulfonate is selected from the group consisting of solutions of sulfuric acid in water, in aqueous methanol, in aqueous ethanol, and in aqueous acetone.

* * * * *